United States Patent [19]
Akins

[11] Patent Number: 5,425,724

[45] Date of Patent: Jun. 20, 1995

[54] AORTIC PERFUSION CANNULA

[76] Inventor: Cary W. Akins, 18 Circle Dr., Dover, Mass. 02030

[21] Appl. No.: 233,052

[22] Filed: Apr. 26, 1994

[51] Int. Cl.⁶ ............................................. A61M 25/00
[52] U.S. Cl. ...................................... 604/284; 604/49; 604/50; 128/772
[58] Field of Search .......... 604/284, 282, 280, 96–100, 604/43, 246, 264, 49, 50; 128/772, 713, 642

[56] References Cited

U.S. PATENT DOCUMENTS

| | | | |
|---|---|---|---|
| 5,112,347 | 5/1992 | Taheri | 604/96 X |
| 5,158,540 | 10/1992 | Wijay et al. | 604/96 X |
| 5,178,158 | 1/1993 | deToledo | 128/772 |
| 5,291,896 | 3/1994 | Fonger et al. | 604/264 X |
| 5,324,260 | 6/1994 | O'Neill et al. | 604/96 |

Primary Examiner—John D. Yasko
Attorney, Agent, or Firm—Fishman, Dionne & Cantor

[57] ABSTRACT

An aortic cannula is presented which comprises two tubes. One of the tubes is for blood perfusion and the other for monitoring arterial pressure. The tubes are outwardly joined yet have distinct lumens at the insertion end of the cannula. The device provides for superior accuracy in monitoring arterial pressure while avoiding complications caused by the Bernoulli principle and peripheral artery monitoring locations.

14 Claims, 2 Drawing Sheets

AORTIC PERFUSION CANNULA

BACKGROUND OF THE INVENTION

1. Field of the Invention

This invention relates to an improved perfusion cannula having a blood pressure sensing arrangement for use in conjunction with cardiopulmonary bypass procedures.

2. Prior Art

The field of cardiac surgery is usually defined as that specialty in the discipline of surgery that involves the operative correction of defects of the human heart. Although some early cardiac surgical operations were performed on the beating heart, the true explosion of the specialty followed the introduction by Gibbon of the pump-oxygenator in 1953. In fact, one could make the case that the field of cardiac surgery for the surgeon is defined by the use of cardiopulmonary bypass with a pump-oxygenator. With the use of this device the entire function of the patient's heart and lungs can be temporarily replaced by a machine, which allows the cardiac surgeon to operate on or in the quiet heart. This advance allowed the operative correction of many diseases that were previously untreatable, and also allowed new, more exact correction of other diseases that had only been partially approachable in the beating heart.

The performance of effective cardiopulmonary bypass requires a cannula (or cannulae) to be placed into the right side of the heart or major veins to drain blood from the patient into the pump-oxygenator. In the pump-oxygenator the blood is then exposed to a gaseous mixture (similar to the function provided by the normal lungs) that eliminates carbon dioxide and adds oxygen to the blood. The oxygenated blood is then usually passed through a heat exchange mechanism that allows the temperature of the blood to be controlled. The oxygenated blood, now cooled or warmed to the desired temperature, is returned to the body through a perfusion cannula. In the early days of cardiac surgery, and in some unusual circumstances today, that cannula is placed into a large peripheral artery, such as the common femoral artery. However, because of a higher incidence of complications associated with that method of blood return to the body, in virtually all cardiac operations today the blood is returned through a cannula placed into the ascending aorta, usually just proximal to the origin of the innominate artery.

The aortic perfusion cannula, which is returning oxygenated blood from the pump-oxygenator, is usually a piece of tapered plastic tubing. The cannula has a small bend in its distal end to direct flow into the lumen of the aorta, even though the cannula itself enters the aorta perpendicularly. The inlet end of the cannula may contain an adapter that allows the cannula to be connected directly to the plastic tubing from the pump-oxygenator that is carrying the blood back to the body.

The insertion of the aortic cannula is usually performed in the following fashion. After the patient's chest has been opened and the pericardium (sac around the heart) has been entered, concentric purse-string sutures are placed into the anterior wall of the ascending aorta just proximal to the origin of the innominate artery. The clear area in the center of the purse-string sutures is made large enough to accommodate the size of the aortic perfusion cannula. A small incision is then made through the wall of the aorta into its lumen in the center of the purse-string sutures. The aortic perfusion cannula is then inserted through that incision into the aorta, clamping the perfusion cannula so that blood will not come out of the aorta. Air is evacuated from the perfusion cannula as it is joined by a connector to the tubing from the pump-oxygenator, so that the entire system is free of any air bubbles. The purse-string sutures are then tightened to prevent the escape of blood from the aorta around the perfusion cannula.

Similar venous drainage cannulae are inserted through purse-string sutures into the right atrium of the heart or directly into the superior and inferior vena cavae for connection to the drainage side of the pump-oxygenator. Cardiopulmonary bypass is instituted by removing the clamps from the venous drainage cannulae, allowing unoxygenated blood which is returning to he right side of the heart to be diverted into the pump-oxygenator. There carbon dioxide is eliminated from the blood, oxygen is added and the temperature of the fluid is adjusted. The oxygenated blood is then pumped into the arterial return side of the pump-oxygenator, through the aortic perfusion cannula, into the patient.

During such a cardiopulmonary bypass procedure, the blood pressure of the patient must be monitored. Monitoring is most often carried out through a small catheter inserted percutaneously into a small peripheral artery, usually the radial artery of the wrist. Unfortunately, measurement of the arterial pressure through a radial cannula is not always accurately reflective of the central aortic pressure because of local resistance changes that can be caused by temperature or pharmacologic agents used during cardiopulmonary bypass procedures. This is a serious drawback to the efficiency and effectiveness of cardiopulmonary bypass procedures in general, since it is vitally important that blood pressure be maintained within a certain acceptable range. When blood pressure is below the acceptable range, perfusion of the organs of the body can be seriously compromised, leading to significant damage; and when the pressure exceeds acceptable limits excessive bleeding and possible organ damage can result. Mismeasurement can also be caused by peripheral arterial vascular disease. Consequently, the present inventor sought an improved arrangement for use with cardiopulmonary bypass procedures. Careful and extensive research led to the discovery of the invention described hereinbelow.

SUMMARY OF THE INVENTION

The above-discussed and other drawbacks and deficiencies of the prior art are overcome or alleviated by the aortic cannula and pressure monitoring device of the present invention.

The invention comprises an aortic cannula sufficient in size to perform perfusion procedures requiring up to 7-8 liters of blood per minute to be pumped. The cannula further comprises an integral pressure measuring arrangement, positioned in a predetermined location, to accurately monitor arterial blood pressure.

The device of the invention is a significant improvement over prior art devices because it prevents the above mentioned drawbacks associated with peripheral arterial pressure monitoring devices and also prevents mismeasurement of blood pressure caused by the Bernoulli principle.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DESCRIPTION OF THE PREFERRED EMBODIMENTS

Figure 1:
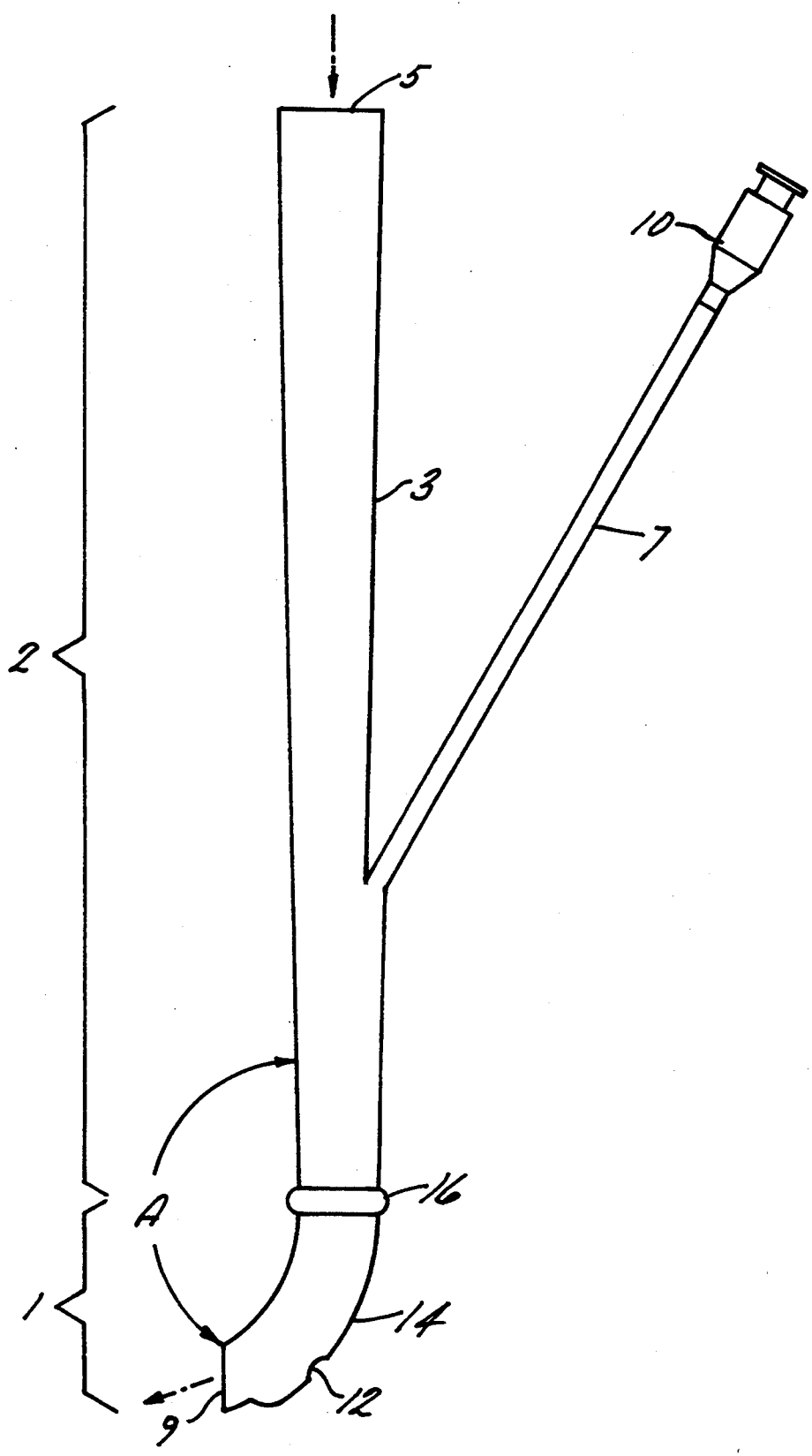
FIG. 1 is a side plan view of the invention.
Figure 2:
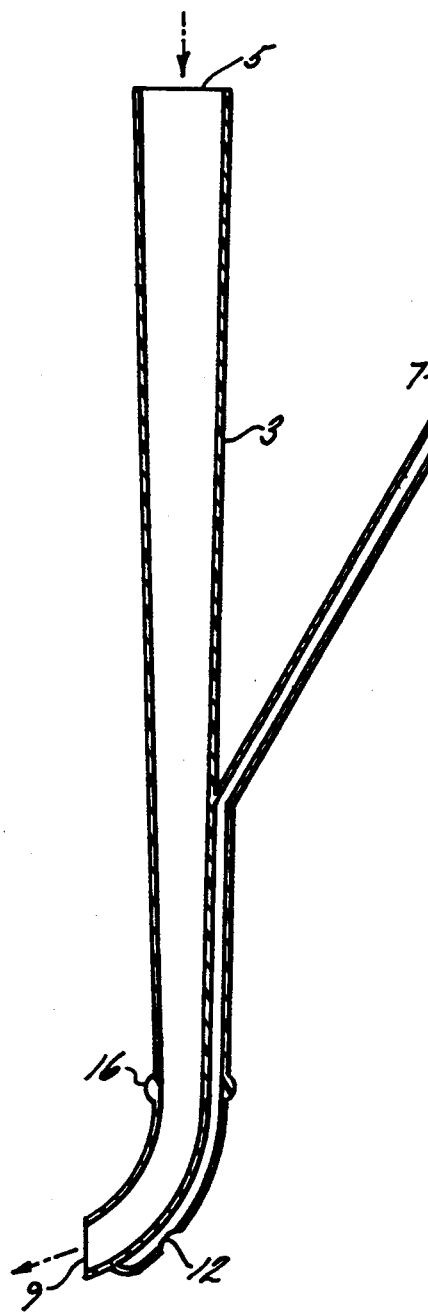
FIG. 2 is a cross-sectional view of the invention.
Figure 3:
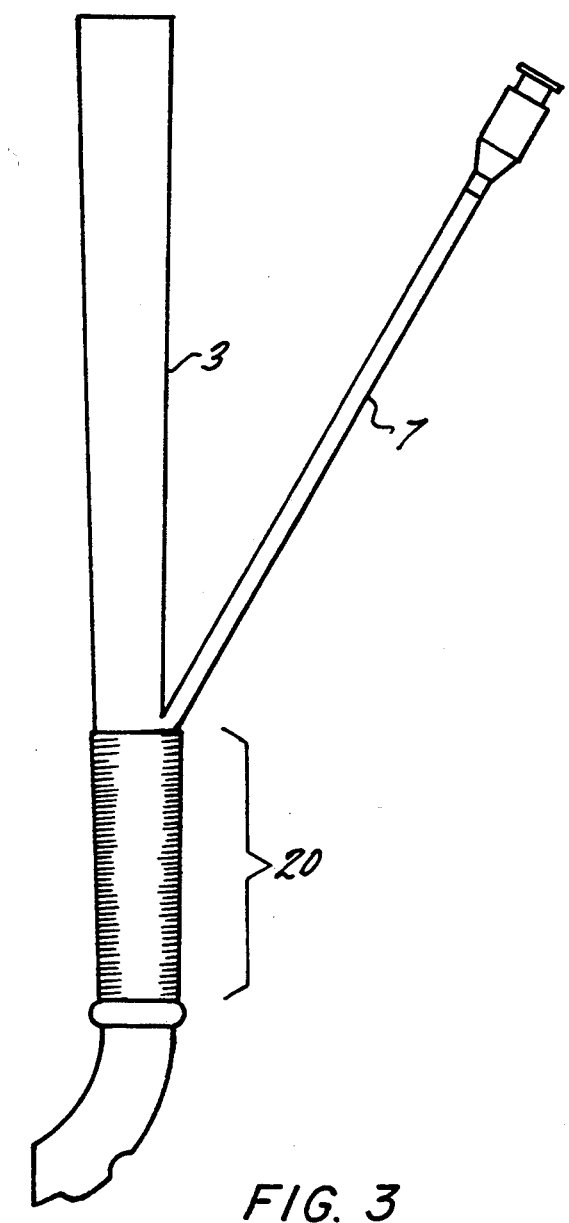
FIG. 3 is an alternative embodiment of the invention.

Referring to FIG. 1 the cannula of the invention includes two broad regions, a first region 1 and a second region 2. The first region of the cannula is for insertion into the aorta or other primary blood vessels in a patient. The first region has the appearance of being one tube but in actuality contains more than one conduit. The second region of the cannula is made up of branching tubes. In the most preferred embodiment two tubes are contemplated. One of the tubes in the preferred embodiment is a perfusion conduit 3 having an inlet orifice 5, while the second tube is a pressure monitoring channel 7.

At the first region 1 where the outer appearance is that of a single tube, the pressure channel 7 is joined to the perfusion conduit 3, however the lumens of the tubes are maintained separate. This arrangement allows for two openings in the first region 1, one of which is perfusion outlet 9, which is the opening of perfusion conduit 3, and the other of which is receiving aperture 12 of pressure monitoring channel 7. Outlet 9 and aperture 12 are critically positioned so that the outlet 9 faces generally in the direction of blood flow and aperture 12 faces substantially against blood flow. The positioning of the lumen openings is considered critical because it is believed that accuracy of the pressure monitoring system is greatly affected by the distance "x" between the outlet 9 and aperture 12. The range of distances which is acceptable for the purpose of this invention is from 5 mm to 15 mm. This measurement is taken along an outside arc of a bend area 14. Where the aperture 12 is positioned outside of the range noted, accuracy of the pressure reading suffers. Where the aperture 12 is positioned too close to collar 16, the thickness of the aortic wall can occlude the aperture thus rendering pressure readings unreliable. Where the aperture 12 is positioned too close to outlet 9, the pressure reading may suffer from turbulence occasioned by the flow through outlet 9.

The bend area 14 enables the perfusion outlet 9 to be oriented perpendicularly to the longitudinal direction of the aorta so that the perfusing fluid is directed axially within the lumen of the aorta. That is not to say that the bend area necessarily is at a 90° angle but merely that the outlet 9 is substantially perpendicular to the axial direction of the aorta's lumen. This can be achieved by manufacturing outlet 9 at an acute angle to the bend area 14, when 90° is not achieved in the bend area 14. The bend area 14 includes an angle (Designated as A in FIG. 1) in the range of 90°–150° with a most preferable angle being 135°.

The pressure monitoring channel measures internal arterial pressure by transmitting that pressure through a fluid-filled column to a strain gauge or piezoelectric pressure transducer. The preferred fluid in the column is heparinized saline. The saline is maintained within the column simply by the interface of the heparinized saline and the heparinized blood in the patient's aorta, diaphragm or other containing arrangements are not necessary. Moreover, it is preferred to utilize no containing arrangement at the interface so that blood from the aorta can easily be aspirated to ensure that no air is trapped in the system. To facilitate such measurement, a Luer adapter 10 is most preferably fitted onto one end of the pressure monitoring channel 5, remote from aperture 12, in the second region of the cannula, to allow additional sterile, fluid-filled tubing to extend outside the sterile operative field for connection to the pressure-monitoring transducer.

Perfusion conduit 3 is preferably tapered with a larger diameter end being the blood inlet orifice 5 and perfusion outlet 9 being the smaller end. The perfusion conduit, most preferably, is constructed of a flexible substance of, for example, plastic or rubber, and measures six to ten inches in length with an inlet orifice diameter of about half an inch and a perfusion outlet 9 of about one quarter to three-eights inch in diameter. In this arrangement seven to eight liters of fluid per minute can be effectively perfused into the patients body without over stressing the pump mechanism. It will be appreciated by one of skill in the art that smaller sizes of the aortic perfusion cannula may be indicated for use on children or smaller adults. The invention is thus not limited to the measurements provided but merely is most preferable when constructed to these specifications.

Another preferred feature of the invention to aid in positioning of the cannula is a collar 16, molded to the cannula adjacent the bend area 14. The collar helps to prevent the cannula from extending too deeply into the ascending aorta.

In an alternate embodiment of the invention, the area 20, between collar 16 and where perfusion conduit 3 and pressure monitoring channel 7 branch, is wrapped with wire to strengthen the area and help prevent bending.

To use the above described cannula, a patient is opened, exposing the chest cavity and the pericardium is entered. A surgeon will then locate the ascending aorta and install "purse-string" sutures, just proximate to the innominate artery. The size of the area defined within the sutures is predetermined so as to be capable of accepting the first region of the cannula. A small incision is then made and the cannula inserted. The purse-string sutures are tightened around the cannula to prevent the escape of blood. It is important, at this point, to evacuate all air from the system to avoid possible air embolism within the patient's body. The cannula is then joined at the inlet orifice 5 to connector tubing from the heart-lung machine. Once all air is evacuated from the system, the pump-oxygenator can be initiated and takes,over the function of the patient's heart and lungs. Subsequently, in most situations, a much smaller cardioplegic cannula is placed in the heart itself to administer cardioplegic agents to cool and silence the electrical activity in the heart. Most procedures would utilize both an aortic perfusion cannula and a cardioplegic cannula, however it will be understood by those skilled in the art that the aortic perfusion cannula of the present invention can be used in some procedures by itself. The cardioplegic cannula on the other hand must be used in conjunction with a perfusion cannula.

The most important benefit of the invention disclosed herein is that it eliminates the necessity for using a peripheral artery pressure measuring device thus avoiding the shortcomings associated therewith. This is particularly beneficial to doctors and patients alike because where arterial pressure is monitored more effectively, it can be maintained more accurately. This will reduce some of the risks associated with cardiac procedures and increase the success rate of these procedures.

While the preferred embodiment has been shown and described, various modifications and substitutions may be made thereto without departing from the spirit and scope of the invention. Accordingly, it is to be understood that the present invention has been described by way of illustrations and not limitation.

What is claimed is:

1. A perfusion cannula comprising:
   a) a blood perfusion conduit having an inlet, an outlet and a lumen; and
   b) a pressure monitoring channel having an inlet aperture, an outlet and a lumen wherein each said blood perfusion lumen and said pressure monitoring lumen remains distinct from the other and wherein the said conduit and said channel are outwardly joined at least at an insertion end of the cannula and said inlet aperture of the pressure monitoring channel is oriented such that it faces substantially against the direction of blood flow in a patient's body.

2. A perfusion cannula as claimed in claim 1 wherein the outlet of the blood perfusion conduit and inlet aperture of the pressure monitoring channel are located at a predetermined distance from one another.

3. A perfusion cannula as claimed in claim 2 wherein the predetermined distance is in the range of about 5 mm to about 15 mm.

4. A perfusion cannula as claimed in claim 1 wherein the conduit is a tapered tube.

5. A perfusion cannula as claimed in claim 1 wherein the cannula is constructed of a flexible material.

6. A perfusion cannula as claimed in claim 1 wherein the conduit has a length in the range of from 6 to 10 inches.

7. A perfusion cannula as claimed in claim 4 wherein the taper is up to 40%.

8. A perfusion cannula as claimed in claim 1 wherein the insertion end of the cannula includes a collar to limit insertion depth into an aorta of a patient's body.

9. A perfusion cannula as claimed in claim 1 wherein the pressure monitoring channel is connected on an outlet end, remote from the insertion end of the cannula, to a Luer adapter.

10. A perfusion cannula as claimed in claim 1 wherein the insertion end of the cannula includes a bend area having an arc in the range from 90° to 150°.

11. A perfusion cannula as claimed in claim 10 wherein the bend area has an arc of 135°.

12. A perfusion cannula as claimed in claim 10 wherein the inlet aperture of the pressure monitoring channel is positioned on an outer arc of the bend.

13. A perfusion cannula as claimed in claim 10 wherein the blood perfusion conduit outlet defines a plane which is located in radial relationship to a patients aorta such that blood pumped through the conduit is released in the proper direction of blood flow of a patient.

14. A perfusion cannula comprising:
   a) a blood perfusion conduit having an inlet, an outlet and a lumen;
   b) a pressure monitoring channel having an inlet aperture, an outlet and a lumen wherein each lumen remains distinct from the other and wherein the conduit and channel are outwardly joined at least at an insertion end of the cannula; and
   c) a stiffening coil of a suitable stiff material said stiffening coil being disposed circumferentially around said aortic perfusion cannula in a region where the conduit and channel are joined.

* * * * *